(12) United States Patent
Bolduc et al.

(10) Patent No.: US 8,980,636 B2
(45) Date of Patent: Mar. 17, 2015

(54) AUTOMATIC TITRATOR

(71) Applicant: Ecolab USA Inc., St. Paul, MN (US)

(72) Inventors: John Wilhelm Bolduc, Eagan, MN (US); Blake Roberts Otting, Bloomington, MN (US); Paul R. Kraus, Apple Valley, MN (US); Robert Ryther, Saint Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 54 days.

(21) Appl. No.: 13/838,409

(22) Filed: Mar. 15, 2013

(65) Prior Publication Data

US 2014/0273244 A1 Sep. 18, 2014

(51) Int. Cl.
*G01N 21/79* (2006.01)
*G01N 31/16* (2006.01)

(52) U.S. Cl.
CPC ..................... *G01N 21/79* (2013.01)
USPC ................. 436/51; 436/50; 436/55; 436/135; 436/163; 436/164; 422/75; 422/82.05; 422/82.09

(58) Field of Classification Search
CPC ....... G01N 21/75; G01N 21/77; G01N 21/78; G01N 21/79; G01N 31/16; G01N 31/166; G01N 31/228; G01N 35/00; G01N 35/00584; G01N 35/00594
USPC ........... 436/43, 50, 51, 52, 55, 127, 135, 163, 436/164; 422/68.1, 75, 81, 82.05, 82.09
See application file for complete search history.

(56) References Cited

U.S. PATENT DOCUMENTS

| | | | |
|---|---|---|---|
| 5,192,509 A | 3/1993 | Surjaatmadja et al. | |
| 5,389,546 A * | 2/1995 | Becket | 436/51 |
| 6,010,664 A | 1/2000 | Johnson et al. | |
| 6,432,661 B1 * | 8/2002 | Heitfeld et al. | 435/27 |
| 7,349,760 B2 * | 3/2008 | Wei et al. | 700/267 |
| 8,076,155 B2 * | 12/2011 | Tokhtuev et al. | 436/164 |
| 8,119,412 B2 * | 2/2012 | Kraus | 436/135 |
| 2002/0151080 A1 | 10/2002 | Dasgupta et al. | |
| 2003/0032195 A1 * | 2/2003 | Roeraade et al. | 436/163 |
| 2003/0129254 A1 * | 7/2003 | Yasuhara et al. | 424/601 |
| 2006/0210961 A1 * | 9/2006 | Magnaldo et al. | 435/4 |
| 2010/0136705 A1 * | 6/2010 | Kojima et al. | 436/129 |

FOREIGN PATENT DOCUMENTS

JP H06-58882 A 3/1994

OTHER PUBLICATIONS

Sully et al. Analyst, vol. 87, 1962, pp. 653-657.*
International Search Report and Written Opinion for International Application No. PCT/US2014/019982, mailed Jul. 7, 2014, 10 pages.

* cited by examiner

*Primary Examiner* — Maureen Wallenhorst
(74) *Attorney, Agent, or Firm* — Fredrikson & Byron, P.A.

(57) ABSTRACT

A system and method for performing automated titrations. An automatic titrator utilizes control devices and sensors adapted for various chemical reactions to perform titrations and determine the content of a desired component of a solution. Batch and continuous mode titrations are possible. Titrant is added to a sample either in varying amounts or rates and a titration endpoint is observed via sensors. Control devices detect when the titration endpoint occurs and calculates the desired content. Various reactions within the solution may be suppressed in order to titrate isolated components individually.

31 Claims, 7 Drawing Sheets

AUTOMATIC TITRATOR

BACKGROUND

Titration is a method well known and practiced to determine concentrations of components of a solution. Titrations of various chemistries are practiced, wherein generally a titrant is added to a solution in which it reacts with select components thereof. Once the entirety of the reacting component has reacted with the known titrant, a measurable or noticeable change occurs, indicating the reaction is complete. In some cases, the noticeable change comprises a color change. Color changes, for example, can vary widely across various chemistries of titrations.

While known as a science, titrations can be a tedious process, requiring careful practice by a chemist or other skilled operator. In some instances, it may be impractical to keep a chemist or other technician on hand to perform titrations, though data acquired by titrations may be desirable. Automated titrators may be implemented which attempt to judge when complete reactions have occurred and the appropriate titration calculations to determine an amount of a component in a solution. However, depending on the reaction, it may be difficult for an automated process to accurately determine an endpoint of a reaction. Additionally, automated systems may require a large amount of time to complete a process, which may be undesirable or unacceptable if a solution needs monitoring at certain time intervals.

SUMMARY

The disclosure is generally related to systems and methods for performing titrations. In certain embodiments of the invention, a sample comprising an unknown amount of a desired component is provided along with a light source and optical sensor comprising a threshold with the sample disposed between them. At least one reagent is added to the sample in order to cause a color change observable by the optical sensor, crossing the threshold thereof. The sample may then be titrated with a titrant until the sample undergoes a second color change, observable by the optical sensor by re-crossing the threshold. The measure of titrant necessary to induce the second color change is determined and the amount of the desired component in the solution is calculated using this measure.

Certain systems of the present invention comprise a reaction vessel into which a sample is contained. A reagent pump transports a reagent into the reaction vessel to facilitate a first color change. The color change is observable by an optical arrangement. A titrant pump is configured to supply titrant into the reaction vessel, the titrant such that, when added in sufficient quantity to the sample and reagent, it facilitates a second color change. The system further can comprise a control device in communication with the optical arrangement, the titrant pump, and at least one reagent pump. The control device can be configured to supply reagent to the sample until the optical arrangement senses the first color change, and can supply titrant to the sample until the optical arrangement senses the second color change. Based upon a quantity associated with supplying the titrant to achieve the second color change, the control device can calculate the content of a component of the solution.

Various systems and methods of the present invention may be used to determine contents of various solutions involving various chemistries. Such systems and methods may comprise either a batch mode or a continuous mode of operation, wherein samples are added to a fixed volume or are continuously flowed through an apparatus, respectively.

DETAILED DESCRIPTION

The following description provides exemplary embodiments of the invention involving systems and methods for determining amounts of oxidizers in samples. The embodiments described do not limit the scope of the invention in any way, but rather serve as examples to illustrate certain elements thereof "Amount," as used herein, refers to a generic measurable quantity such as mass, concentration, volume, etc. Where applicable, like reference numerals will be used to describe like components, though these components need not be identical.

Figure 1:
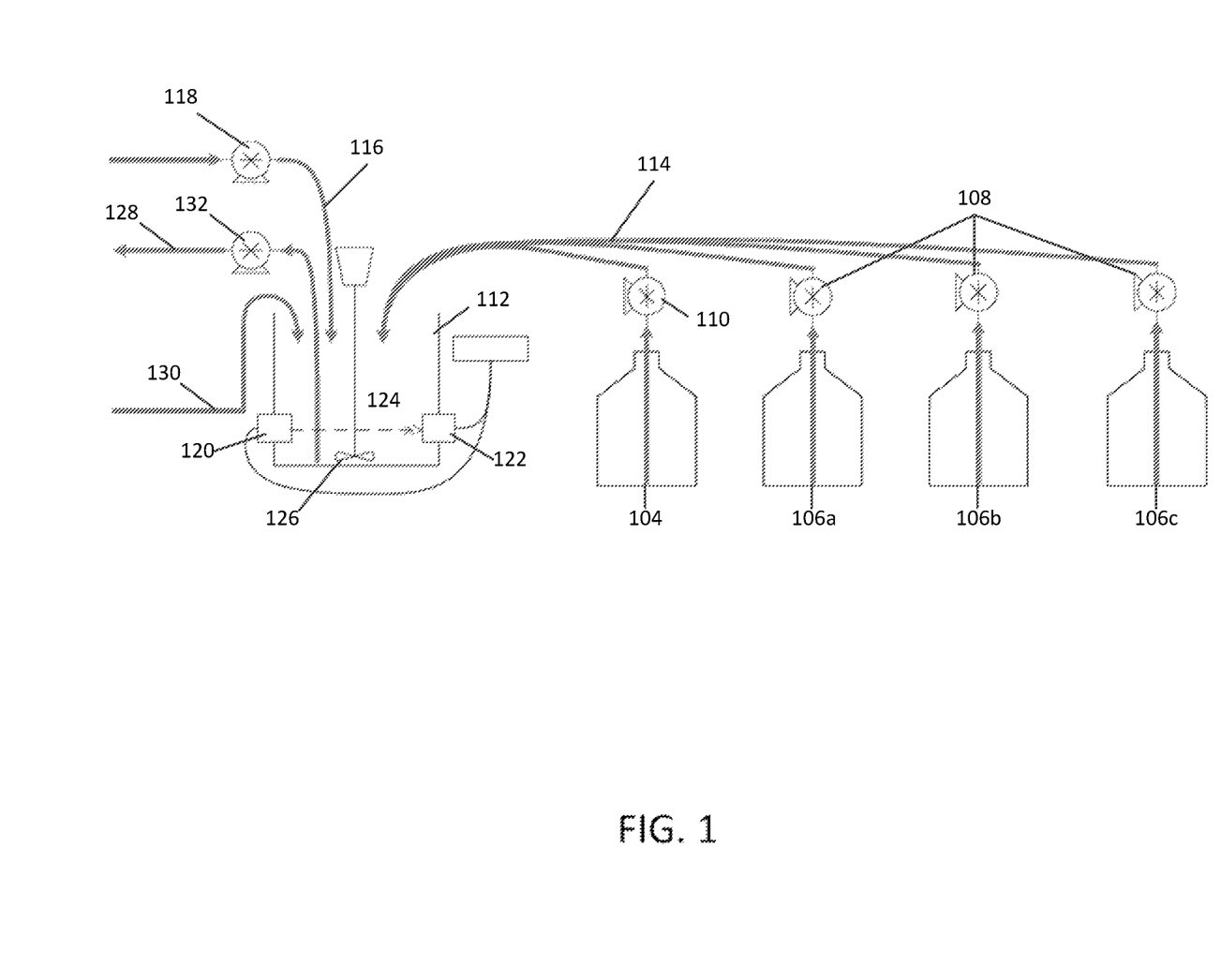
FIG. 1 shows an exemplary diagram of an embodiment of a titration system.

FIG. 1 shows an exemplary diagram of an embodiment of a titration system. FIG. 1 illustrates a batch-mode automatic titrating assembly configured to combine a sample, three reagents, and a titrant. The assembly comprises a series of four storage vessels, each configured to hold a reservoir of certain materials. In this embodiment of the invention, one vessel contains a titrant 104, such as sodium thiosulfate. The remaining three vessels contain a first 106a, second 106b, and third reagent 106c, respectively, selected to react with the sample in a particular way. Reagents may comprise materials such as potassium iodide (KI), a weak acid such as acetic acid, and a starch indicator. The contents of the vessels are in fluid communication with transport means, such as reagent 108 and titrant pumps 110, designed to transport the contents into a reaction vessel 112. In some embodiments of the invention, the same type of pump may be used on each vessel; however in other embodiments it may be preferable to employ alternative pumps for the titrant and the reagents, for example. This may be because a greater degree of precision and control is required of the pump supplying the titrant as compared to the reagents.

To send any of the reagents or titrant to the reaction vessel 112 during operation, an associated pump withdraws the desired chemical from its particular storage vessel and sends it to the reaction vessel 112 via an associated hose 114. According to some embodiments of the invention, hoses 114 from each pump and associated with each material may run separately into the reaction vessel 112. Alternatively, the hoses 114 may combine prior to the reaction vessel 112 in which case the materials in the hoses 114 combine prior to entering the reaction vessel 112, in a manifold for example. In yet further embodiments, select materials may combine while others remain isolated prior to entry into the reaction vessel 112.

A sample inlet hose 116 in communication with a sample pump 118 is shown leading into the reaction vessel 112. Through this arrangement, a sample to be analyzed is brought into the vessel 112. The sample pump 118 may be configured in some embodiments to provide a discrete amount of sample into the reaction vessel 112. In addition, an optical arrangement such as a light source 120 and optical sensor 122 may be implemented in such a way so that the light source 120 projects radiation 124 through the reaction vessel 112, with the optical sensor 122 detecting the radiation on the other side. Of course, in this arrangement, it is necessary that the reaction vessel 112 permit at least some transmission of the radiation from the light source 120 therethrough. Also shown in the embodiment of FIG. 1 is a mixer 126, configured to, when activated, effectively mix together the materials inside the reaction vessel 112. An evacuation hose 128 is also shown in the present embodiment, designed to remove material from the reaction vessel 112. This may be done via suction by utilizing, for example, an evacuation pump 132 to withdraw material from the reaction vessel 112. In some embodiments, a water line 130 may be available to rinse the reaction vessel 112 after use. In such embodiments, water is sent into the reaction vessel 112 via the water line 130, where it dilutes and/or rinses material present in the reaction vessel 112. Then, evacuation hose 128 may evacuate the rinse water and/or dilute sample from the reaction vessel 112.

In its general operation, an assembly such as the one in FIG. 1 may be used to titrate a sample to determine, for example, the amount of oxidizing components therein. In an exemplary embodiment, a discrete amount of sample is first brought into the reaction vessel 112 via the sample inlet hose 116 and sample pump 118. The light source 120 sends radiation through the reaction vessel 112 and sample and is sensed by the optical sensor 122. Next, reagents KI, acetic acid, and a starch indicator are added to the reaction vessel 112 via associated reagent pumps 106 and hoses 114. The sample and the reagents are mixed by the mixer 126, and the combination of the oxidizers present in the sample and these reagents cause the solution to turn a dark blue-black color. The acetic acid is optionally added to assure a slightly acidic resultant sample, but it not always necessary to achieve the desired color change.

Because of this color change, the radiation 124 from the light source 120 is prevented from penetrating the solution, and so it is attenuated prior to reaching the optical sensor. In some embodiments of the invention, the light is completely blocked and is no longer sensed by the optical sensor 122. In other embodiments, the light may be attenuated such that the light sensed at the sensor 122 falls below a threshold level. As such, the sensor can be either analog and/or digital, either providing a gradient of opacity of the sample and/or a digital trip point within the measurement indicating the sample is either clear or opaque. In alternative embodiments, the optical sensor may detect changes of the sample from one color to another instead of changes in the opacity of the sample. In an even further embodiment, the optical sensor can comprise an array detector disposed to simultaneously monitor a band of wavelengths, which may be advantageous for various color changes among various chemistries.

Next, a titrant such as sodium thiosulfate is added to the reaction vessel 112. The mixer continues mixing the solution as more titrant is added. Meanwhile, the radiation 124 from the light source 120 is continually blocked from reaching the optical sensor 122 by the dark-colored sample. Once sufficient titrant has been added, however, the solution changes from the dark color to a clear/transparent color, thereby allowing the radiation 124 to pass through and reach the optical sensor 122. If this second color change persists, titration is complete. If the sample reverts back to a dark color within a small amount of time, further titrant must be added to complete titration. Once titration is complete, the amount of titrant added may be used to calculate the amount of oxidizing components in the sample by typical titration calculation. After the titration is complete, the reaction vessel 112 may be rinsed, for example with water or additional sample solution, and evacuated using the evacuation hose 132.

Figure 2:
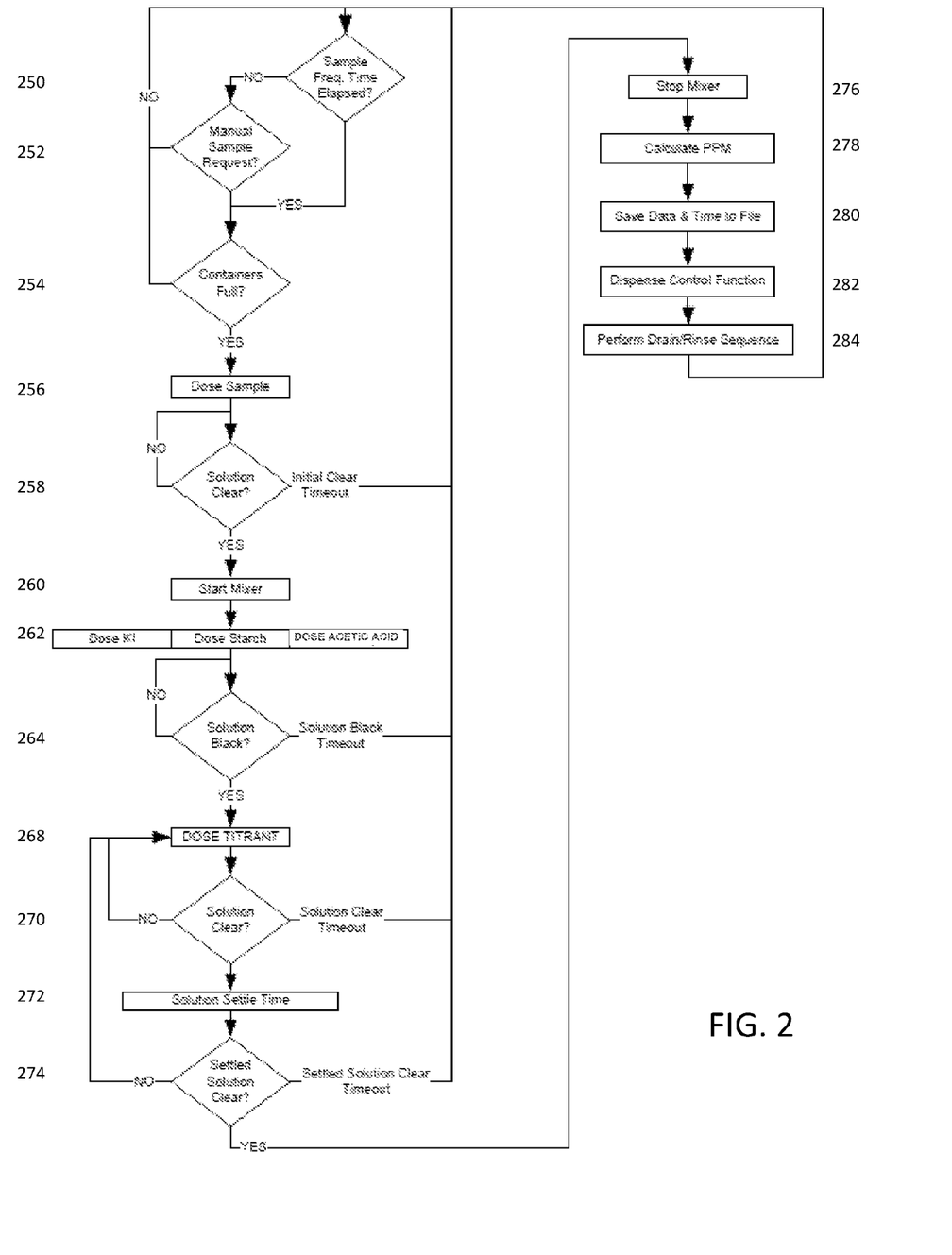
FIG. 2 is a process flow diagram showing steps performed by an embodiment of the present invention.

While described above as something of a typical titration procedure, any or all of the steps above may be automated using, for example, a microcontroller or a programmable logic controller (PLC). While described in various examples as a PLC, alternative automated embodiments of the invention may comprise any device capable of measurements, logical analysis, and control, including device-specific circuitry. The automation may follow the steps of FIG. 2. FIG. 2 is a process flow diagram showing steps performed by an embodiment of the present invention. The process of FIG. 2 may represent the PLC or other automated logic according to some embodiments of the invention.

In a PLC-controlled embodiment of the invention, the PLC first determines if a sample analysis is requested, for example a measurement of oxidizing component of the sample. A measurement may either be requested automatically 250, wherein analysis may be performed on a preprogrammed schedule, or may be requested manually 252. Once a request is received, the PLC determines if the reagent and titrant containers/vessels are full 254. If so, the procedure continues, and the sample solution is brought 256 into the reaction vessel. The PLC then may utilize sensors with which it is interfaced such as the light source and sensor described previously to determine if the solution is transparent 258. If not, and doesn't become so, the system will time out and reset. However, upon sensing a transparent solution, the PLC may start 260 the mixer, then dose 262 the reagents into the reaction vessel with the sample using the aforementioned pumps, for example. The PLC may dose the reagents in a discrete or continuous manner until the optical sensor no longer senses radiation from the light source through the sample, indicating that the sample has changed color. Thus the light source and sensor arrangement may act as a feedback mechanism to the PLC, indicating when sufficient reagent has been added to induce a color change. In some embodiments, the reagents are added in excess so that the amount of oxidizing components in the sample is the limiting factor in the color change. If the PLC fails to sense 264 a color change, it again may time out and reset.

Once the PLC has determined the sample has changed color, and overdosed the sample with reagent if desired, the PLC doses 268 titrant into the reaction vessel using the titrant pump, for example. Preferably, the titrant is added in very small, discrete amounts so that the PLC knows how much titrant has been added at any time. Once again, the light source and optical sensor may act as a feedback mechanism, determining 270 and communicating to the PLC whether the solution in the reaction vessel has reverted to a transparent state. If not, more titrant is added. Once the PLC receives signal that the solution is transparent, it pauses 272 for a solution reaction time, allowing the portion of the desired reaction to react completely. If the solution turns back to a dark color, more titrant is added until the solution can remain 274 transparent throughout the solution reaction time.

Once the solution remains transparent, the PLC may stop 276 the mixer and calculate 278 the amount of oxidizing component present in the sample based upon the amount of titrant necessary to change the solution back to transparent. In some embodiments, the PLC may save 280 this data along with the date and time recorded to a file in memory, and further may itself act as a feedback mechanism to a device that can control the makeup of the sample. For example, if, after calculating an amount of oxidizing component in the sample, the PLC determines that the amount is above or below some threshold, it may signal 282 to an external control device to manipulate the sample until its oxidizing components reach a desired level. Finally, the PLC may drain and rinse 284 the reaction vessel in preparation for the next titration. The process is such that it may be implemented anywhere, such as at a sampling point in a processing facility or other industrial or commercial location not conducive to regularly performing standard titrations. Additionally, the entire process may be completed in a short time; approximately 2 minutes and 40 seconds according to some embodiments. Prior to rinsing and preparing the system to take another measurement, amount may be determined in less time; approximately 1 minute and 20 seconds in some embodiments.

It should be appreciated that in the preceding description, when the PLC is said to have performed an action such as dosing or rinsing, it need not necessarily be the PLC itself to have performed the action. Rather, it is meant that the PLC initiates the action, potentially sending signals to additional equipment such as the aforementioned pumps and optical sensor. Moreover, the PLC may be configured to communicate any results by sending data via a communication network such as Wi-Fi.

The above procedure may be modified in order to extract additional data concerning the types of oxidizers within the sample. For example, in a sample comprising an unknown quantity of peracids and peroxides, the process may be performed with a cooled sample in order to suppress the reaction of the peroxide. This may be done using an ice bath, a pre-cooled sample, or by some other cooling means, such as thermo-electric cooling, for example. Preferably, to suppress the peroxide reaction, the temperature is of the sample is kept at or below around the temperature range of 40-50° F. Once the sample is cooled, the process may be run as above, though the peroxide will not contribute to the titration because of the reduced temperature. Thus, the resulting calculated concentration of oxidizing components will be representative of the peracid concentration of the sample.

Next, to achieve a measure of the peroxide concentration, a strong acid, such as sulfuric acid, and a catalyst, such as ammonium molybdate, may be added. The catalyst and acid will react with the peroxide and cause the solution to once again turn dark, and may be added in excess to assure the color change. The dark solution may once again be titrated to a transparent endpoint using the same titrant as with the peracid procedure, only this time the additional amount of titrant needed will yield the peroxide concentration of the sample, since the peracid had already been titrated. Thus, some embodiments of the invention may comprise cooling means in order to reduce the sample temperature, such as a heat exchanger. Alternatively, depending on the environment of use, the solution may naturally be cooled, for example flume water for produce may be maintained at a cool temperature for purposes other than select titration. Accordingly, in such an arrangement, a cooling mechanism is not necessary to suppress the peroxide reaction.

The transparent to dark blue-black reaction described resulting from the chemistry mentioned above is especially advantageous in the automated process described. Such a stark change in appearance enables a more reliable and accurate determination of the endpoint of the reaction. The described arrangement of a light source and optical sensor detecting radiation from the source through the sample allows for effective determination of a dark vs. transparent sample, thus working particularly effectively with the chemistry described. In some embodiments, the optical sensor may be set with a threshold or trip point, wherein it determines the sample to be transparent once a predetermined amount of radiation from the light source is detected through the sample. In such an embodiment, the sample is treated as a binary system wherein the sample is either transparent or not, and once transparency is determined (and persists), an endpoint is reached. While a sample that changes from dark to transparent during titration has been described, the reverse is also possible, wherein a transparent sample becomes dark during titration. An equivalent arrangement with alternative logic may be used to automate such titrations, as similar analog and/or digital optical arrangements can be used with determined threshold levels being crossed from a direction opposite the previous embodiment.

In alternative embodiments, the optical sensor may signal transparency once it senses any radiation from the light source. Such embodiments may be utilized if the color change is sufficiently stark, such as the blue-black to transparent as described above, for example. It should be noted, however, that with proper optical equipment, such a stark color change may not be necessary in order for the optical arrangement to be able to accurately detect a titration endpoint. In such embodiments, not all reagents may be necessary. For example, the starch indicator may be omitted with the inclusion of certain optics in the optical arrangement.

The embodiments described thus far have comprises what may be described as batch mode titrations, wherein a discrete amount of sample has been isolated and titrated, possibly multiple times, to determine the concentrations of oxidizers in that particular volume of sample. Alternatively, a similar method may be implemented in a continuous mode of operation, wherein a sample flows continuously and is analyzed without isolating any discrete portion of the sample. Instead, the sample flow rate is determined and/or controlled to be a known value.

Figure 3:
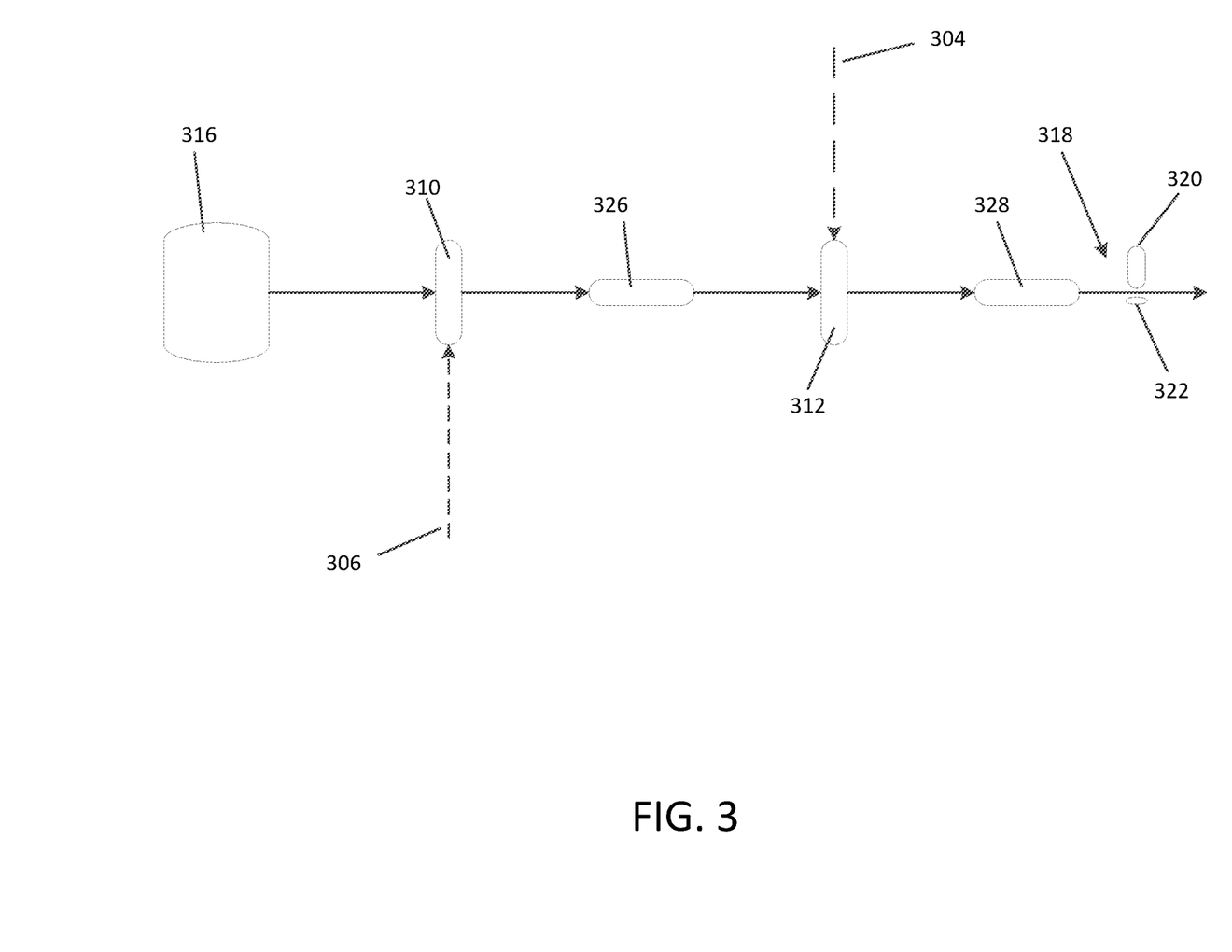
FIG. 3 is a schematic diagram of a continuous-mode automatic titrator.

FIG. 3 is a schematic diagram of a continuous-mode automatic titrator. Here, the sample 316 flows through a line, which may referred to as a reaction vessel—analogous to the component of the same name in the batch mode process, at some known rate into a first manifold 310, where it encounters reagents 306 that combine with the sample 316. In some embodiments, the chemistry described above may be utilized, and a sufficient addition of reagents 306 will cause the sample 316 to turn a dark blue-black color. In this continuous-mode operation, however, the determining factor of "sufficient addition of reagents" corresponds to the rate of reagent addition. This is because the sample 316 is flowing through the system continuously so fresh sample 316 is continuously fed into the first manifold 310. Accordingly, if the reagents 306 are added too slowly, they will fail to adequately react with the entire sample 316 and the sample 316 may not change color. Put another way, in a given amount of time, a certain volume of sample 316 will flow through a particular point in the system. In order to achieve the desired color change, then, there needs to be an appropriate volume of reagent 306 that also flows past this point during the same time, which corresponds to a sufficient flow rate. The sample 316 and reagents 306 may be mixed in a mixer 326.

Thus, in some embodiments of the invention, an excess flow rate or reagent 306 is used in order to assure that the amount of sample flowing is the limiting factor in the reaction to cause the color change. This is analogous to utilizing an excess volume of reagent in batch-mode as has been previously discussed. Once the sample 316 and reagents 306 have combined in the first manifold 310 to form a dark blue-black solution, this solution continues to flow through the system. Some embodiments of the invention comprise an optical arrangement 318, such as a light source 320 and an optical sensor 322, which senses radiation emitted from the light source 320 after it travels through the solution path. Embodiments of the optical arrangement include those already described. Accordingly, in some embodiments of the invention, the optical arrangement 318 may determine whether or not the solution has sufficiently turned a blue-black color before attempting a titration. This may be sensed by a user in a manual operation or may be controlled by a PLC in an automated arrangement so described previously with regard to batch mode. In some embodiments, if the solution is sensed as having not turned to a dark color, the flow rate of the reagents may be increased or sample decreased in order to increase the reagent-to-sample ratio. Alternatively, the lack of a color change may trigger an alarm to cease operation of the system, possibly indicating that the reservoir of one or more reagents may have run out or that the sample lacks the oxidizing element expected to be therein.

In some embodiments, once the sample 316 and reagents 306 have mixed, and the resulting solution has been determined to have undergone a color change, titrant 304 may be added, using a second manifold 312, for example. In some embodiments, titrant 304 may be mixed in to the solution by a mixer 328. Similarly to the incorporation of reagents 306, the flow rate of the titrant 304 is analogous to the amount of titrant added to the sample in batch mode. Again, the same chemistry as described above may be used. Therefore, at an appropriate flow rate of titrant 304 into the flowing solution, the titration should reach and endpoint resulting in a color change. However, to reach a meaningful endpoint yielding accurate results, the lowest flow rate resulting in viewing the color change must be used. This is because if the flow rate of the titrant 304 is too high (i.e. above the minimum to achieve color change or other noticeable endpoint), the characteristic of the endpoint may still be observed. For example, the addition of too much sodium thiosulfate in the batch mode described above will still result in a transparent sample even though an excess of titrant was used, since the same endpoint could have been achieved at a lesser dose.

Thus, in some embodiments of the invention, the flow rate of the titrant 304 is started low, below the flow rate that will result in a color change. The flow rate is then increased until an endpoint is observed, for example by the optical arrangement 318 mentioned above. As was the case with the batch mode, a color change must persist for a certain amount of time without reverting to be considered the true endpoint. Thus, a second optical arrangement may be placed further downstream, for example 20-30 seconds, to assure the color change persists over time. In order to create such a delay in time without utilizing an excess of space, a coil may be used through which to flow the solution. Such measurements may be performed quickly, possibly being completed in less than one to two minutes.

Also similarly to the batch mode process described above, this process will generally yield a concentration of oxidizers present in the sample. However, if the sample is chilled, the reaction of the peroxide will be suppressed, therefore allowing for the determination of the peracid concentration in the sample. Thus, a chilled sample may be used in the continuous process to suppress peroxide reactions and calculate a peracid concentration. In some configurations, the sample is already chilled for purposes other than titration, and the peroxide reaction may be suppressed without need for further chilling. In other embodiments, other chilling means may be employed into the system to intentionally cool the sample.

Once a chilled sample has been titrated to determine a peracid concentration, a catalyst (such as the aforementioned ammonium molybdate) and strong acid (such as sulfuric acid) may be substituted for the weak acid in the combination of reagent. As previously described, the mixing of such components into the sample will cause the peroxide reaction to no longer be suppressed, allowing for both peracid and peroxide reactions. It is noteworthy that in the continuous mode, as time progresses, fresh sample is continuously brought into the system. As a result, despite possibly already determining a peracid concentration using a chilled sample, subsequent titrations including the catalyst and strong acid will involve reactions from both the peroxide and the peracid, since in the fresh sample, the peracid has not undergone a reaction. This is contrary to the batch mode, wherein after determining the peracid content, only the peroxide was left to react.

Thus, when titrating a solution of sample and reagents including a catalyst and strong acid, the amount of oxidizer that will be calculated will comprise both peracid and peroxide together. Accordingly, the difference between the total oxidizer concentration and the peracid concentration (calculated previously by suppressing the peroxide reaction) will yield the peroxide concentration of the sample. In some embodiments, both reactions (with weak acid and with a strong acid and catalyst) may be performed in succession, and in any permutation, since fresh sample is continuously used by the system. In other embodiments, the reactions may be done in parallel, wherein the sample is split into two lines and titrated. One in which peroxide reaction is suppressed and one in which it is not. Simultaneous measurement of peracid and total oxidizer concentrations may then be performed, and a subtraction step will additionally yield the peroxide concentration. It should be noted that, while cooling the sample can advantageously suppress the peroxide reaction in the embodiments described above, temperature changes may have alternative effects on alternative chemistries and titrations, as well as on viscosities and flow rates of components used in, for example, a continuous flow process.

Figure 4A:
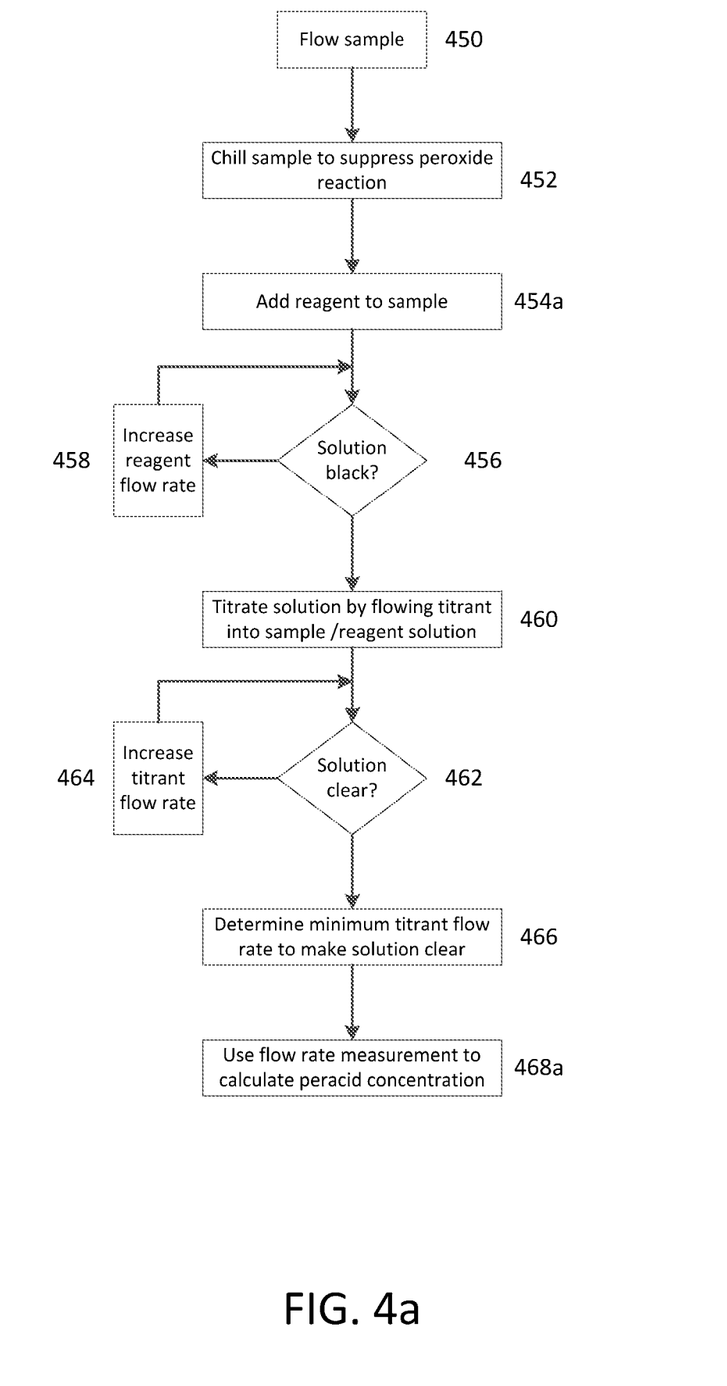
FIG. 4a is a process flow diagram for calculating peracid concentration of a sample using an automated continuous flow embodiment of the invention.
Figure 4B:
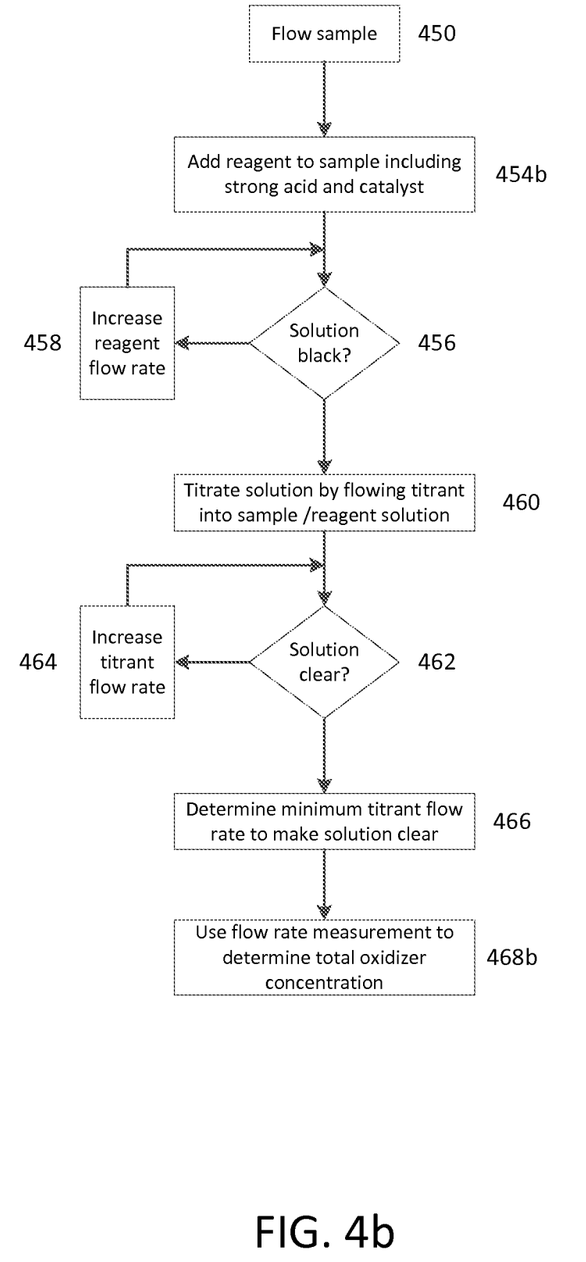
FIG. 4b is a process flow diagram for calculating the total oxidizer concentration of a sample using an automated continuous flow embodiment of the invention.
Figure 4C:
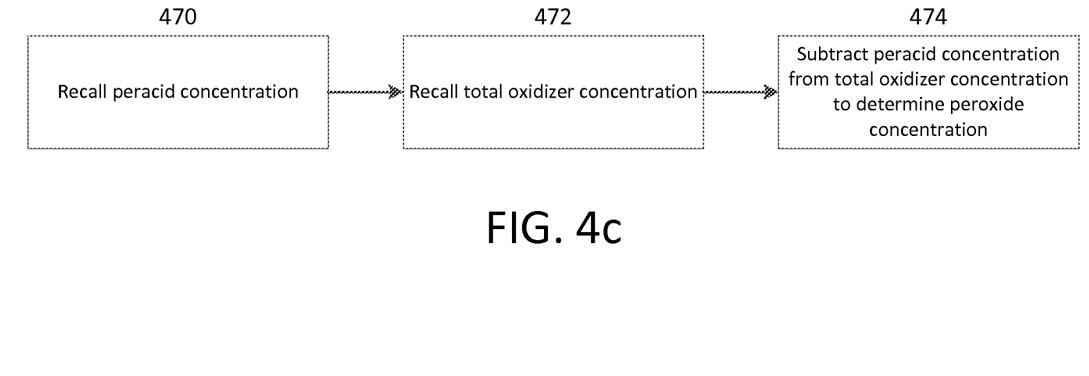
FIG. 4c is a process flow diagram for calculating the peroxide concentration of a sample suing an automated continuous flow embodiment of the invention.

In any of these embodiments, the process may be automated by a controller such as a PLC, using the same or similar feedback mechanisms as the automated batch mode process. FIGS. 4a-4c show process flow diagrams of an automated continuous flow embodiment of the present invention. FIG. 4a is a process flow diagram for calculating peracid concentration of a sample using an automated continuous flow embodiment of the invention, performed, for example, by a PLC. First, the solution flows 450 through the system and is chilled 452 to suppress peroxide reactions. Next the PLC commands pumps to add 454a reagent to the sample while monitoring the color using the optical arrangement, for example. If the solution fails to turn black 456, the PLC calls for an increase 458 in the reagent flow rate. Once the solution is black, the PLC gives orders to titrate 460 the solution by flowing a titrant into the sample/reagent solution while again monitoring the color. If the solution fails to turn clear 462, the PLC calls for an increase 464 in titrant flow rate. Once the solution has turned clear, the PLC determines 466 the minimum titrant flow rate to result in a clear solution. Using this flow rate, the PLC calculates 468 the peracid concentration of the sample.

FIG. 4b is a process flow diagram for calculating the total oxidizer concentration of a sample using an automated continuous flow embodiment of the invention. This process is very similar to that described in FIG. 4a. The process of FIG. 4b is missing the step of chilling 452 the sample to suppress the peroxide reaction, and modifies the step of adding 454a reagents, this time adding 454b reagents including a strong acid and a catalyst to promote peroxide reactions. The rest of the process follows similarly, until the end, at which point the PLC calculates 468b the total oxidizer concentration in the sample.

FIG. 4c is a process flow diagram for calculating the peroxide concentration of a sample using an automated continuous flow embodiment of the invention. This process simply involves recalling 470 the calculated peracid concentration from FIG. 4a, recalling 472 the calculated oxidizer concentration of FIG. 4b, and subtracting the first from the second to calculate 474 the total peroxide concentration of the sample. Thus, following the procedures of FIGS. 4a-4c, the peroxide and peracid concentrations of a sample may be determined. It should be noted that in order to perform the process outlined in FIG. 4c, the processes of FIGS. 4a and 4b must first be performed. However, as discussed previous, due to the continuously flowing nature of the continuous mode embodiment, they may be performed in any order or even simultaneously.

Generally, analysis using the continuous mode may be done more quickly than using the batch mode. Additionally, it allows for fast and convenient "double check" type calculations. This is because that, once the titrant flow rate is brought from below the endpoint of the titration to above, the solution turns clear, and a concentration is calculated, the titrant flow rate may be brought back down through the endpoint, at which point the solution flowing should turn back to the dark color. Thus, a second calculation of the concentration may be performed quickly after the first, enabling for a second measurement to ensure accuracy or to monitor rapid changes in the concentration. Note that also if the solution turns clear upon immediate addition of the titrant, the titrant flow rate may be reduced in order to determine the endpoint of titration. Alternatively, the sample flow rate may be changed instead of or in addition to the flow rate of the titrant in order to determine the endpoint.

One possible difficulty in the continuous method is that the titrant flow rate may be changed by an inconvenient amount to achieve a desired endpoint. For example, if a sample has heavy concentrations of peracid and/or peroxide, yet the flow rate of titrant is increasing at a very slow rate, it may require a large number of rate increases to arrive at the endpoint, wasting time and chemicals as they flow through the system and nothing happens. Conversely, if a sample has very low concentrations of peracid and peroxide, but the flow rate of the titrant is changed very rapidly, it may be very difficult to resolve an accurate endpoint.

One solution to this problem employed by certain embodiments of the invention is to increase the flow rate of the titrant by an amount that is nonlinear over time. An exponential increase in flow rate, for example, will begin by making small changes in the flow rate while the concentrations involved are small. Over time, as the concentrations become larger (since the flow rate has continued to increase), small changes in flow rate become unnecessarily precise compared to the concentrations at hand and the flow rate may increase by larger amounts. In such an embodiment, a low concentration of peroxide and peracid may be accurately resolved by the small changes in concentrations early in the process, while large concentrations of peracid and/or peroxide may be titrated in a shorter amount of time since the rate of titrant addition increases more rapidly over time.

Figure 5:
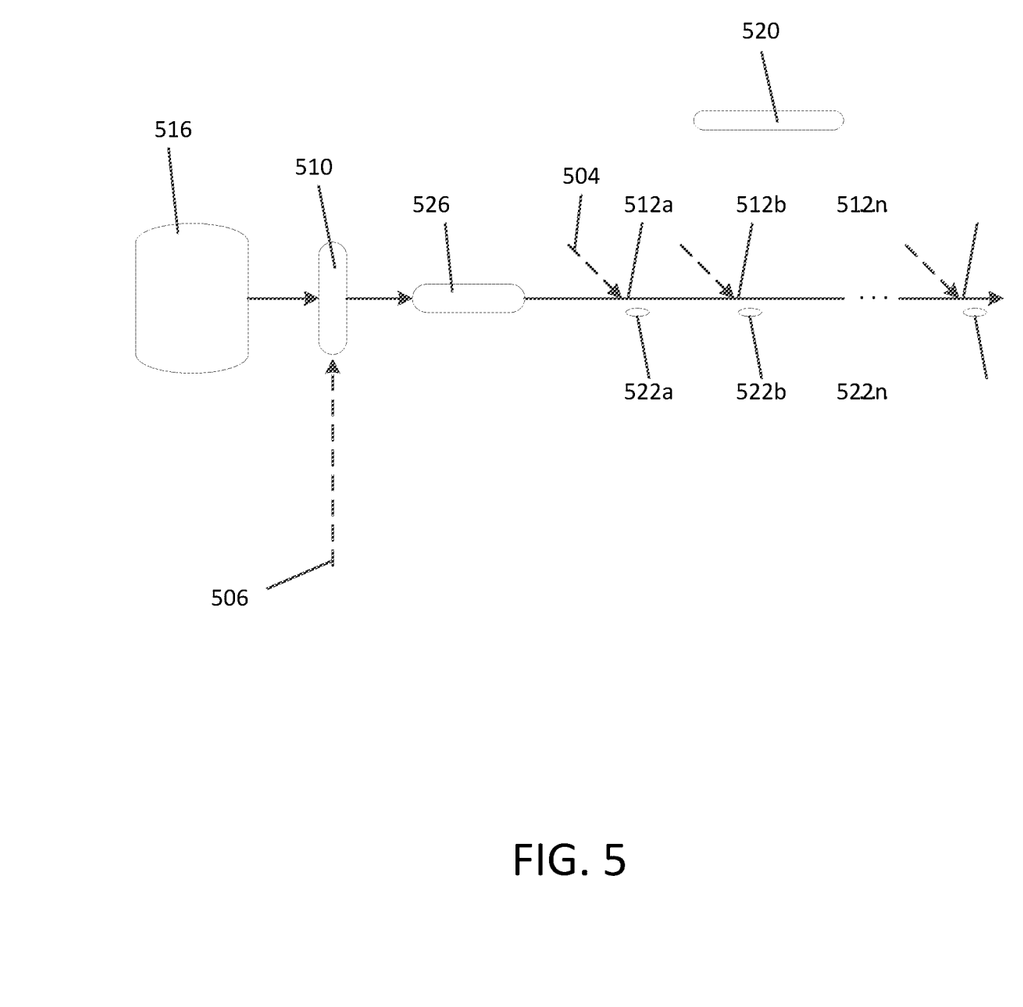
FIG. 5 is a schematic diagram of an alternative embodiment of the invention comprising multiple titrant injection points.

In alternative embodiments of the invention, multiple injection points of the titrant may be included in the system in order to determine the endpoint of the reaction. FIG. 5 is a schematic diagram of an alternative embodiment of the invention comprising multiple titrant injection points. In this embodiment, sample 516 flows and mixes with reagents 506, possibly in a mixer 510. The titrant 504 is added at multiple titrant injection points 512a . . . 512n in the flow path of the solution, with optical sensors 522a . . . 522n arranged nearby and downstream from each injection point 512. After each subsequent addition, the amount of titrant in the solution increases, and the solution is monitored by the optical sensor 522. Accordingly, after a certain number of injection points, a sufficient amount of titrant to reach the endpoint may be reached and will be sensed by the optical sensor 522 disposed after the injection point 512 causing the endpoint to be reached. The combined flow rate of titrant at the endpoint may be determined and the desired sample concentration calculated.

In a similar yet still alternative embodiment, multiple titrant injection points may be disposed along a line in which a solution comprising the sample and reagent is flowing. According to the exemplary chemistry described above, this solution may be dark in color. In some embodiments, each injection point 512 may have associated with it an optical sensor 522 for measuring a parameter such as color or intensity of light emitted from a light source 520 on the other side of the line through which the sample is flowing. Each optical sensor 522 is located downstream from its associated injection point 512. Such an arrangement is possible with a single or with multiple light sources 520 providing light to the sensors.

In this embodiment, as sample flows through the line, titrant is added at each injection point 512, the flow rate of the titrant differing between points. Thus, similarly to the previously described embodiment, a sufficiently high titrant flow rate will result in the sample being completely titrated and changing color. If, at any particular injection point 512, titrant is injected at a sufficiently high flow rate, the solution immediately at or after the injection point 512 will undergo the color change associated with that titration.

The system may be configured so that the optical system comprising the light source 520 and plurality of optical sensors 522a . . . 522n can detect the color change associated with the titration. Thus, if the color change happens at a particular injection point 512, the optical sensor 522 associated with that point can sense the occurrence of the endpoint of the titration and indicate that the titrant flow rate at that particular injection point 512 is at least sufficient to titrate the sample. If an array of injection points 512a . . . 512n is used with each point having a different titrant flow rate, it can be determined that the flow rate corresponding to the endpoint of titration lies between the highest flow rate not resulting in titration and the lowest flow rate that does result in titration. Smaller differences in flow rates between injection points 512a . . . 512n will lead to a more accurate determination of the flow rate corresponding to the titration endpoint. Once this flow rate is determined, the methodology described above can be used to calculate the concentration of the desired component of the sample.

An advantage of this method is that, with a fast enough optical arrangement, the analysis at each injection point can be done very quickly. Thus, only a small amount of titrant needs to be added at each point to determine whether or not the flow rate is sufficient for complete titration, and an overall small amount of titrant is needed to determine an endpoint. This process may be automated by a device such as a PLC in similar ways as described relating to alternative embodiments, wherein the controller may control the flow rates of the sample and titrants, detect the titration by means of the optical arrangement, and calculate the concentration from the flow rates. In this embodiment, the controller performs the additional task of determining a "cut-off" point, above which titration occurred and below which it did not.

It is further within the scope of the invention, including any embodiments herein described, to include a method for calibrating the system. Calibration steps can be performed in-line, calibrating flow rates, measurements, and the like. In some embodiments, calibrations can be performed prior to every titration to provide increased accuracy to the measurement. In other embodiments, a calibration can be performed after a predetermined number of measurements, or can be prompted by a user. In-line calibrations can be performed without substantially slowing down the analysis procedure. Such calibration may include injection of a sample of known concentration and confirming that the system measures the concentration accurately. To the extent the measurement is inaccurate, the system could self-adjust in order to accurately measure the sample of known concentration.

Various embodiments have been described. Combinations of elements described may additionally form alternative embodiments of the invention. These and others are within the scope of the following claims.

The invention claimed is:

1. A method for determining the amount of a desired component in a solution, the method comprising:
providing an amount of sample;
providing a light source and an optical sensor with the sample disposed there between, the optical sensor comprising a threshold value;
adding to the sample at least one reagent so that the sample undergoes a first color change and causes a measurement by the optical sensor to cross the threshold value in a first direction,
adding a titrant to the sample over time with a controlled titrant pump;
increasing the amount of titrant added to the sample at a rate that is nonlinear with time until the sample undergoes a second color change wherein the measurement by the optical sensor crosses the threshold value in a second direction opposite the first;
determining a measure of the titrant necessary to induce the second color change; and
calculating, using the determined measure, the amount of the desired component in the solution.

2. The method of claim 1, wherein, when the sample undergoes a first color change, the sample blocks light from the light source from being detected by the optical sensor.

3. The method of claim 2, wherein, when the sample undergoes a second color change, the sample no longer blocks light from the light source from being detected by the optical sensor.

4. The method of claim 1, wherein the step of increasing the amount of titrant added to the sample at a rate that is nonlinear with time until the sample undergoes a color change comprises nonlinearly increasing the flow rate of the titrant in a continuous process.

5. The method of claim 4, wherein the flow rate of the titrant is increased exponentially over time.

6. The method of claim 4, wherein the determined measure of the titrant comprises the flow rate of the titrant.

7. The method of claim 6, wherein the titrant is added at a plurality of injection points through a continuous flow of sample, each injection point associated with an optical sensor, and wherein a plurality of titrant flow rates are injected to the sample from the plurality of injection points, and wherein the flow rate at each subsequent injection point increases nonlinearly.

8. The method of claim 7, wherein the optical sensor associated with each injection point comprises a portion of an array of optical sensors.

9. The method of claim 8, wherein the light source comprises a single light source.

10. The method of claim 1, wherein the amount of desired component in the solution comprises the amount of oxidizer in the solution.

11. The method of claim 10, wherein determining the amount of oxidizer in the solution comprises determining at least the amount of peracid, and further comprising the step of suppressing peroxide reactions in order to determine the amount of peracid in the sample.

12. The method of claim 11, wherein the step of suppressing peroxide reactions comprises cooling the sample.

13. The method of claim 11, further comprising the steps of:
adding to the sample a catalyst to promote peroxide reactions and inducing a third color change in the sample, blocking light from being detected by the optical sensor;
adding the titrant to the sample until the sample undergoes a fourth color change and allows the light from the light source to be detected by the optical sensor;
determining a second measure of the titrant necessary to induce the fourth color change; and
calculating the amount of peroxide in the sample based upon the second measure.

14. The method of claim 13, wherein the amount of peracid and amount of peroxide in the sample are calculated substantially simultaneously.

15. The method of claim 13, wherein the catalyst comprises ammonium molybdate.

16. The method of claim 1, further comprising:
supplying a calibration sample of known amount;
titrating the calibration sample to determine a calculated amount;
comparing the calculated amount to the known amount to determine a calibration error;
performing a calibration step so that the calibration error between the calculated amount and the known amount is corrected; and
applying a calibration correction to the calculated amount of the desired component based on the performed calibration step.

17. The method of claim 1, further comprising adjusting the amount of the desired component in the solution when the calculated amount is outside a predetermined threshold range of the amount.

18. A system for determining the peracid content in a sample, the system comprising:
a first reaction vessel for containing a first volume of the sample;
at least one reagent in fluid communication with the first reaction vessel, the reagent such that when applied to the sample it facilitates a first color change;
at least one reagent pump associated with the reagent and configured to transport the reagent to the first reaction vessel;
a first optical arrangement for detecting a color change of a species in the first reaction vessel;

a titrant in fluid communication with the first reaction vessel, the titrant such that when applied to the combined sample and reagent in sufficient quantity facilitates a second color change;

at least one titrant pump associated with the titrant configured to transport the titrant to the first reaction vessel;

a control device in communication with the first optical arrangement, the at least one titrant pump and at least one reagent pump, and configured to supply reagent to the first volume of sample contained in the first reaction vessel via the at least one reagent pump until it senses, via the first optical arrangement, the first color change;

supply titrant via the at least one titrant pump to the sample and reagent combination in the first reaction vessel in an amount which increases at a rate that is nonlinear with time until it senses, via the first optical arrangement, the second color change; and calculate, based on a controlled quantity associated with supplying the titrant and the amount of titrant supplied to induce the second color change in the first reaction vessel, the peracid content in the sample.

19. The system of claim 18, further comprising:

a second reaction vessel arranged in parallel with the first reaction vessel and configured to receive and contain a second volume of the sample, the second volume of sample being separate from the first volume;

a second optical arrangement for detecting a color change of a species in the second reaction vessel;

at least one reagent pump configured to transport the reagent to the second reaction vessel;

a catalyst and a catalyst pump associated therewith for transferring the catalyst to the second reaction vessel to facilitate peroxide reactions in the second reaction vessel; and at least one titrant pump associated with the titrant and configured to transport the titrant to the second reaction vessel; wherein the control device is in communication with the second optical arrangement, the at least one reagent pump configured to transport the reagent to the second reaction vessel, the catalyst pump for transferring the catalyst to the second reaction vessel, and the at least one titrant pump associated with the titrant and configured to transport the titrant to the second reaction vessel, and is configured to supply the sample to the second reaction vessel;

supply the reagent to the sample in the second reaction vessel until it senses, via the second optical arrangement, the first color change;

supply the catalyst via the catalyst pump to the second reaction vessel to promote peroxide reactions within the second reaction vessel;

supply the titrant at a prescribed and controlled quantity via the at least one titrant pump top the sample, reagent and catalyst combination in the second reaction vessel until it senses, via the second optical arrangement, the second color change; and calculate the peroxide content in the sample based on a controlled quantity associated with supplying the titrant, the amount of titrant supplied to induce the second color change in the second reaction vessel, and the peracid content in the sample.

20. The system of claim 19, wherein the sample is cooled to a sufficiently low temperature to suppress peroxide reactions in the first reaction vessel; and wherein the catalyst supplied to the second reaction vessel facilitates peroxide reactions in a cooled sample.

21. The system of claim 19, wherein the controlled quantity associated with supplying the titrant comprises a flow rate of the titrant.

22. The system of claim 21, wherein the system is a continuous flow system, and wherein the first reaction vessel and the second reaction vessel are arranged in parallel in the continuous flow system.

23. The system of claim 19, wherein the first color change is from transparent to a blue-black color.

24. The system of claim 19, wherein the first optical arrangement comprises a light source and an optical sensor with the first reaction vessel disposed there between.

25. The system of claim 24, wherein the optical sensor comprises an array of sensors, each sensor being sensitive to a particular wavelength or band of wavelengths.

26. The system of claim 19, wherein the at least one reagent comprises potassium iodide and starch.

27. The system of claim 19, wherein the control device comprises a programmable logic computer, and is configured to transmit data over a communication network.

28. The system of claim 19, wherein the peracid content can be determined within about 1 minute and 20 seconds.

29. A method for determining the concentration of oxidizer in a transparent sample, the method comprising;

continuously flowing the sample through a reaction vessel;

detecting, using an optical arrangement, the transparency of the sample;

adding to the sample at a first manifold at least one reagent such that the combination of the reagent and the sample produces a first solution;

adding a titrant to the first solution to form a second solution;

observing at least one optical property of the second solution using an optical arrangement;

changing the flow rate of at least one of the sample or the titrant in a first direction until the optical property of the second solution sufficiently changes from a first state to a second state;

determining a first flow rate of the changed flow rate of the at least one of the sample and the titrant at which the change from the first state to the second state occurred;

calculating, using the first flow rate, a first measurement of the concentration of oxidizer in the sample;

changing the flow rate of the at least one of the sample or the titrant in a second direction, the second direction being opposite the first, until the optical property of the second solution sufficiently changes from the second state to the first state;

determining a second flow rate of the changed flow rate of the at least one of the sample and the titrant at which the change from the second state to the first state occurred; and calculating, using the second flow rate, a second measurement of the concentration of oxidizer in the sample.

30. The method of claim 29 wherein the steps are performed or initiated by a programmable logic computer.

31. The method of claim 29, wherein the optical arrangement comprises an array detector for detecting light.

* * * * *